United States Patent
Tregub et al.

(10) Patent No.: US 7,383,723 B2
(45) Date of Patent: Jun. 10, 2008

(54) DETECTING PARTICLE AGGLOMERATION IN CHEMICAL MECHANICAL POLISHING SLURRIES

(75) Inventors: Alexander Tregub, Oak Park, CA (US); Mansour Moinpour, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 0 days.

(21) Appl. No.: 11/137,674

(22) Filed: May 24, 2005

(65) Prior Publication Data

US 2006/0266736 A1   Nov. 30, 2006

(51) Int. Cl.
*G01N 15/06* (2006.01)
*G01N 11/00* (2006.01)

(52) U.S. Cl. .................. 73/61.71; 73/54.02; 73/866

(58) Field of Classification Search .............. 73/61.42, 73/61.71, 54.02, 64.41, 866
See application file for complete search history.

(56) References Cited

U.S. PATENT DOCUMENTS 6,390,179 B1 * 5/2002 Yasrebi et al. .............. 164/519

OTHER PUBLICATIONS

Lortz, W. et al. "News from the M in CMP- Viscosity of CMP Slurries, a Constant?", Material Reasearch Society Symposium Proceedings, vol. 767, 2003, pp. F1.7.1-F1.7.10.*

* cited by examiner

*Primary Examiner*—Daniel S. Larkin

(57) ABSTRACT

A method for detecting particle agglomeration in CMP slurries. In accordance with an implementation of the invention, a CMP slurry is tested for abrasive particle agglomeration by applying an ultra high shearing force to the slurry and analyzing its rheological behavior. Through the comparison of slurry rheological behavior, implementations of the invention make it possible to detect particle agglomeration in a slurry and to distinguish between fresh and aged slurries.

24 Claims, 4 Drawing Sheets

US 7,383,723 B2

DETECTING PARTICLE AGGLOMERATION IN CHEMICAL MECHANICAL POLISHING SLURRIES

BACKGROUND

Chemical mechanical polishing (also known as chemical mechanical planarization or CMP) is a semiconductor manufacturing process that uses an abrasive, corrosive slurry in conjunction with a polishing pad to planarize the microscopic topographic features on a partly processed wafer so that subsequent processes can begin from a flat surface. CMP is also used in damascene processes to define features, such as interconnects and vias. The planarization process relies on both physical grinding as well as chemical reactions that often occur between the material being polished and components of the slurry.

The abrasive particles within a CMP slurry tend to agglomerate over time, even during storage at room temperatures. The quality of a CMP slurry therefore deteriorates as it ages. This agglomeration of abrasive particles diminishes the quality of the resulting polish by affecting the polish uniformity and increasing the wafer defect rate. Furthermore, a CMP slurry is subjected to high shearing during a CMP process due to the rotation of the polishing pad and wafers and due to the small gap between the pad and the wafer. This shearing can irreversibly change slurry properties and also affect CMP performance.

It would be advantageous to develop a process by which the age of a CMP slurry can be determined, thereby allowing aged slurries to be discarded before they affect the quality of a wafer polishing process. The current state of the art viscosity metrology does not detect particle agglomeration.

DETAILED DESCRIPTION

Described herein are systems and methods of detecting particle agglomeration in CMP slurries. In accordance with an implementation of the invention, a CMP slurry is tested for abrasive particle agglomeration by applying an ultra high shearing force to the slurry and analyzing its rheological behavior. Through the comparison of slurry rheological behavior, implementations of the invention make it possible to distinguish between fresh and aged slurries.

In the following description, various aspects of the illustrative implementations will be described using terms commonly employed by those skilled in the art to convey the substance of their work to others skilled in the art. However, it will be apparent to those skilled in the art that the present invention may be practiced with only some of the described aspects. For purposes of explanation, specific numbers, materials and configurations are set forth in order to provide a thorough understanding of the illustrative implementations. However, it will be apparent to one skilled in the art that the present invention may be practiced without the specific details. In other instances, well-known features are omitted or simplified in order not to obscure the illustrative implementations.

Various operations will be described as multiple discrete operations, in turn, in a manner that is most helpful in understanding the present invention, however, the order of description should not be construed to imply that these operations are necessarily order dependent. In particular, these operations need not be performed in the order of presentation.

Figure 1:
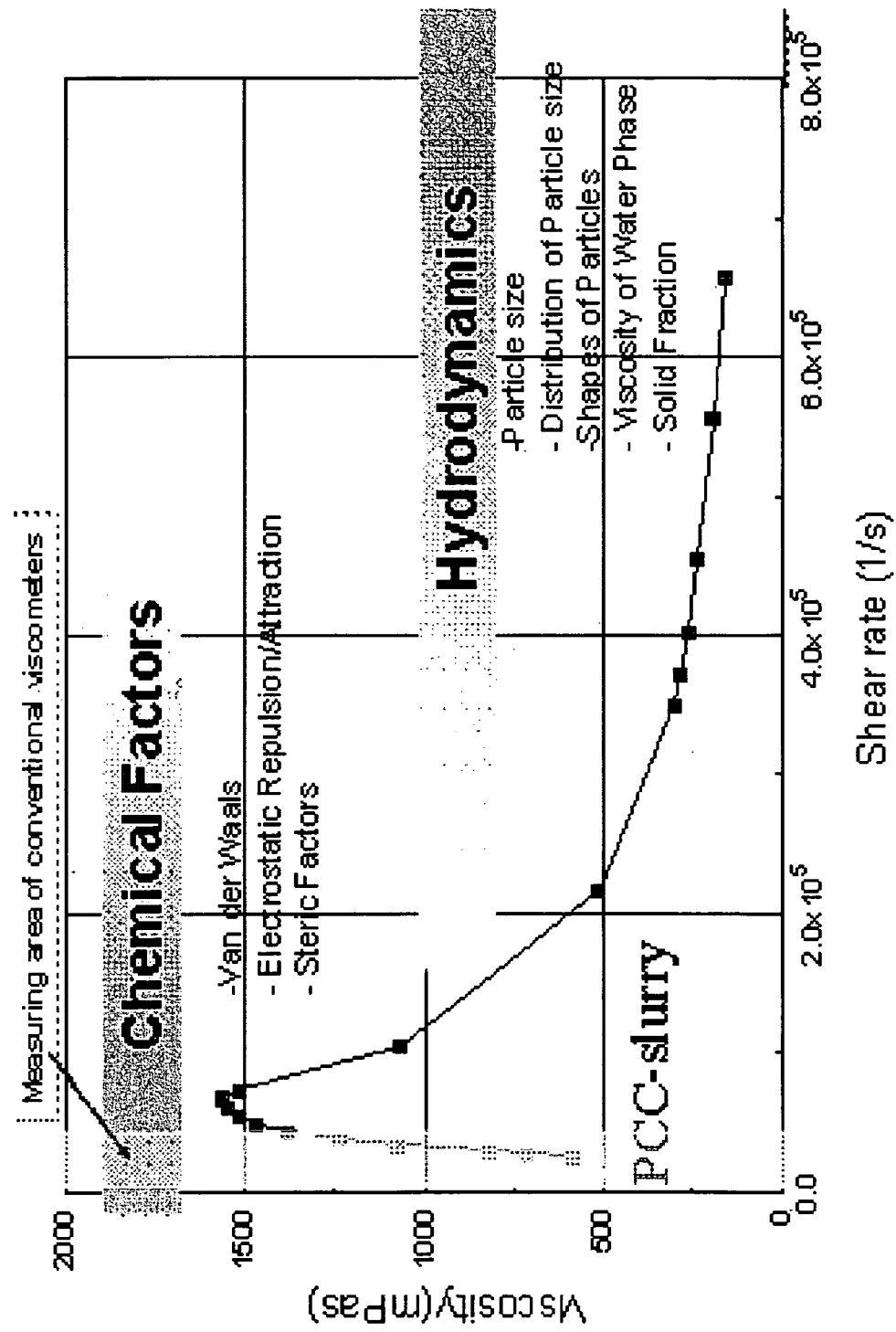
FIG. 1 illustrates which molecular factors become predominant at different shear rates.

It has been shown that shearing CMP slurries at conventional shear rates cannot enable the detection of particle agglomeration. One reason for this is because different molecular forces and interactions become dominant at different shear rates. FIG. 1 illustrates which factors are predominant at conventional shear rates and which factors are predominant at ultra high shear rates.

At conventional shear rates of up to $2.0 \times 10^4$ $sec^{-1}$, such as the shear rates used by conventional viscometers and rheometers, the predominant factors are chemical factors, such as Van der Waals forces, electrostatic repulsion, electrostatic attraction, and steric factors. As shear rates increase to ultra high shear rates, however, the predominant factors become hydrodynamic factors, such as particle size, particle size distribution, particle shape, viscosity of the water phase, and the solid fraction. The agglomeration of abrasive particles in the CMP slurry contributes to the hydrodynamic factors and therefore may be detected using ultra high shear rates.

Figure 2:
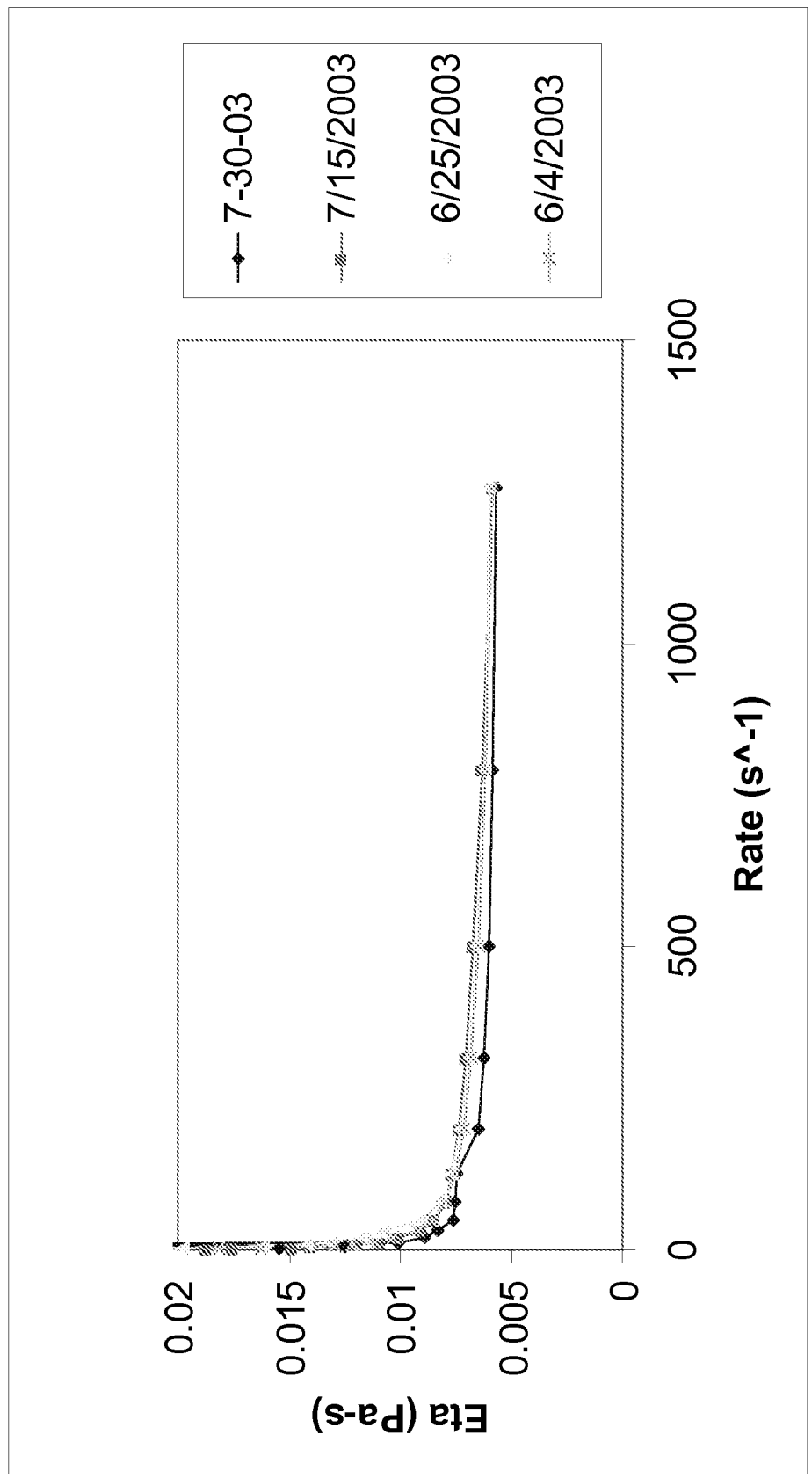
FIG. 2 is a graph of data from rheometric tests conducted on four CMP slurries at conventional shear rates.

FIG. 2 shows rheometric tests on four CMP slurries at conventional shear rates of up to 1500 $sec^{-1}$. All four CMP slurries tested were fumed silica slurries. One was a fresh slurry with 25% solids, one was aged for over a month with 25% solids, one was fresh with 10% solids, and one was aged for over a month with 10% solids. As shown in FIG. 2, there are substantially no differences in the rheological behavior of the CMP slurry aged for longer than one month compared to the fresh CMP slurry. All four slurries behaved similarly, and all four slurries showed thinning rheological behavior. As explained in FIG. 1, the hydrodynamic factors associated with particle agglomeration in the aged slurries had no effect on the rheometric tests conducted at conventional shear rates. Accordingly, the four CMP slurries in FIG. 2 have substantially similar rheological behavior, regardless of age.

The aged CMP slurries used to provide the data shown in FIG. 2 were stored at room temperature in thermal conditioning laboratory room for longer than one month. The viscosity of the slurries was measured using an Advanced Rheometric Expansion System (ARES) dynamic rheometer by TA Instruments, Inc. of Piscataway, N.J.

As the shear rate is increased above conventional shear rates, for example to medium shear rates that range from 15,000 $sec^{-1}$ to 25,000 $sec^{-1}$, there is still little difference in the rheological behavior of aged slurries and fresh slurries. Both types of slurries still tend to have similar viscosities, and both types of slurries still tend to show similar thickening behavior.

In accordance with an implementation of the invention, ultra high shear rates may be used to analyze the rheological behavior of CMP slurries to determine whether a CMP slurry suffers from particle agglomeration, as is generally the case with aged slurries. In implementations of the invention, ultra high shear rates include shear rates that range from $1.0 \times 10^5$ $sec^{-1}$ to $5 \times 10^6$ $sec^{-1}$. In some implementations, the ultra high shear rate may range from $4.0 \times 10^5$ $sec^{-1}$ to $1.5 \times 10^6$ $sec^{-1}$.

The ultra high shearing force may be applied to the CMP slurry using any known processes. For instance, to develop ultra high shearing, an ultra high shear rate rheometer may be used in implementations of the invention. The ultra high shear rate rheometer may operate based on pushing slurry flow through a small opening, such as a small slit, where in some implementations the slit width may range from 0.01 mm to 1.0 mm. The ultra high shear rate rheometer may alternately operate based on pushing slurry flow through a capillary tube, where in some implementations the capillary diameter may range from 0.1 mm to 2.0 mm and the capillary length may range from 5 mm to 20 mm. The actual dimensions of the slit or the capillary tube may vary based on the slurry viscosity, abrasive particle size and content, and shearing force or flow rate.

In implementations of the invention, ultra high shear rate rheometers that may be used to analyze CMP slurries include, but are not limited to rheometers manufactured by Coivu, Inc. of Duluth, Ga.

Figure 3:
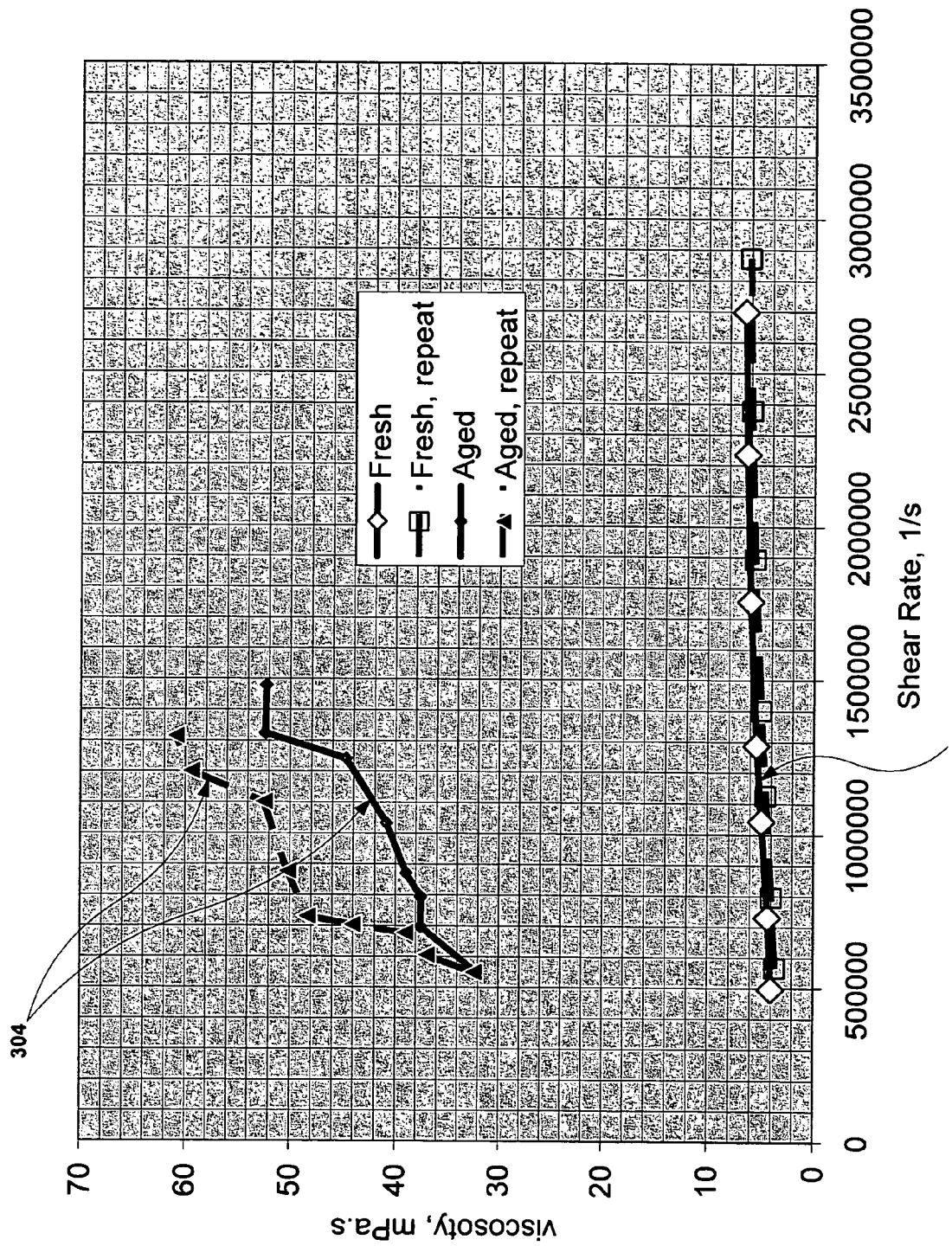
FIG. 3 is a graph of data from rheometric tests conducted on two CMP slurries at ultra high shear rates.

FIG. 3 shows the rheological behavior of a fresh CMP slurry 302 and an aged CMP slurry 304 at ultra high shear rates. As shown, the fresh CMP slurry 302 exhibited very different rheological behavior than the aged CMP slurry 304. The CMP slurries used in FIG. 3 were colloidal silica slurries and the aged CMP slurry 304 was stored for approximately 1.5 months. At these ultra high shear rates, the hydrodynamic factors now become very dominant and cause a significant change in viscosity to occur.

The fresh CMP slurry 302 had a relatively low viscosity at the ultra high shear rates, and that viscosity mildly rose as the ultra high shear rate increased. The fresh CMP slurry 302 therefore exhibited mild thickening behavior. When a second rheometric test was conducted on the fresh CMP slurry 302, the results were substantially similar to the first rheometric test.

Unlike the fresh CMP slurry 302, the aged CMP slurry 304 had a relatively high viscosity value at the ultra high shear rates. As shown in FIG. 3, the aged CMP slurry 304 had an initial viscosity (at an ultra high shear rate of $5.0 \times 10^5$ sec$^{-1}$) that was approximately eight times that of the fresh CMP slurry 302. And further unlike the fresh CMP slurry 302, as the ultra high shear rate increased, the viscosity of the aged CMP slurry 304 substantially increased. In fact, the viscosity of the aged CMP slurry 304 nearly doubled as the ultra high shear rate increased from $5.0 \times 10^5$ sec$^{-1}$ to $1.5 \times 10^6$ sec$^{-1}$. Therefore, the aged CMP slurry 304 exhibited strong thickening behavior. When the rheometric test was conducted a second time on the aged CMP slurry 304, the rheological behavior of the aged slurry 304 was similar to the first test and still remarkably different than that of the fresh CMP slurry 302. The primary difference during the second test was that as the ultra high shear rate was increased, the thickening behavior of the aged CMP slurry 304 was less dramatic than in the first test.

Although the test results in FIG. 3 were for a specific type of CMP slurry, it has been shown that the viscosity of aged CMP slurries at ultra high shear rates above $5.0 \times 10^5$ sec$^{-1}$ may be 1.5 to 5 times higher than the viscosity of fresh CMP slurries at the same ultra high shear rates, depending on slurry type. It has also been shown that aged CMP slurries show thickening behavior at the ultra high shear rates, as evidenced in FIG. 3.

In accordance with an implementation of the invention, ultra high shear rates are used to probe slurry properties as viscosity measurements at ultra high shear rates allow distinguishing between aged and fresh CMP slurries. The aged slurries may then be discarded instead of being used in a CMP process.

Figure 4:
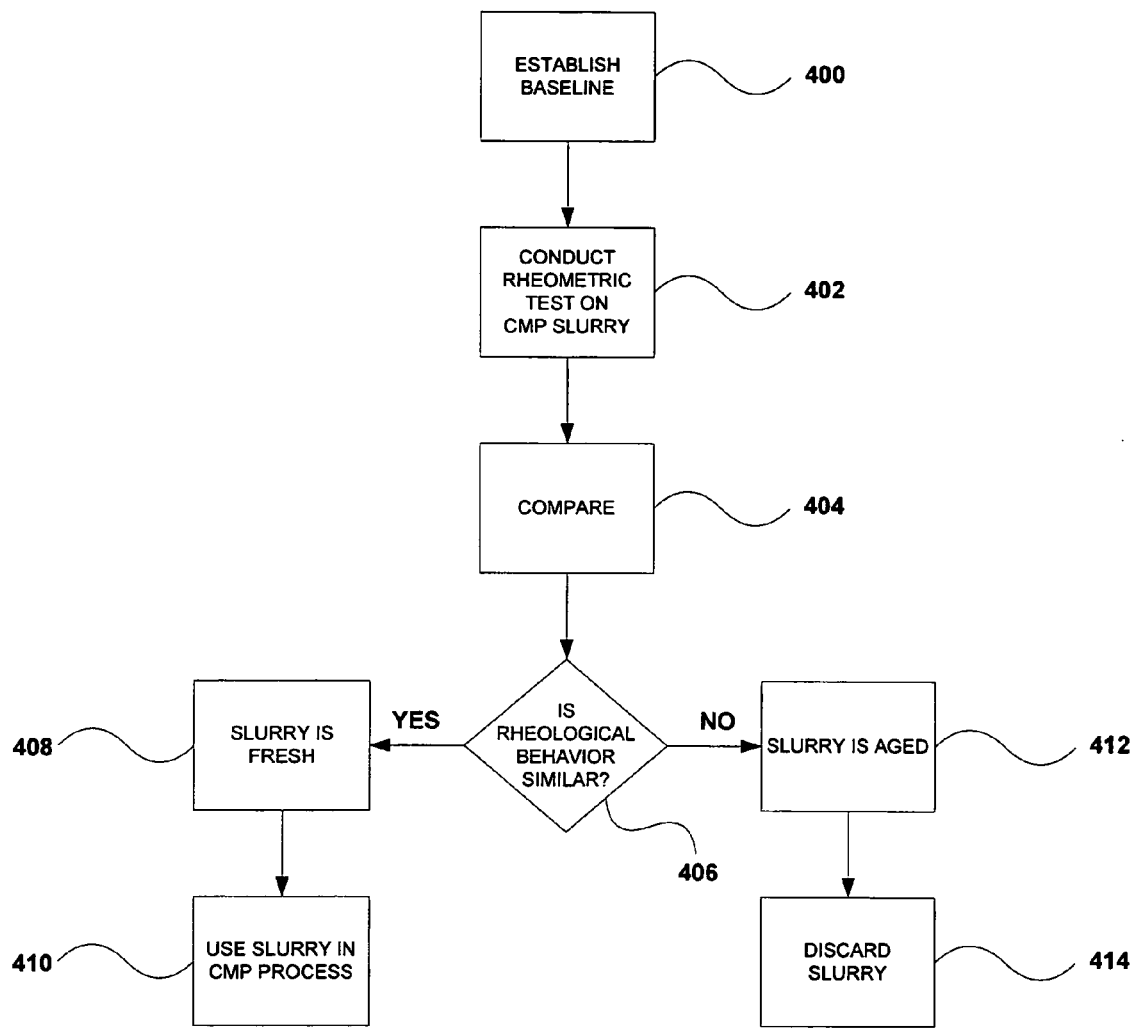
FIG. 4 is a method to analyze a CMP slurry in accordance with the invention.

FIG. 4 illustrates one implementation of a method by which CMP slurries may be analyzed for particle agglomeration. A baseline of rheological behavior may be established for a specific CMP slurry (400). The baseline may be determined by conducting rheometric tests on fresh samples of the specific CMP slurry with shear rates greater than $1.0 \times 10^5$ sec$^{-1}$. In some implementations, the shear rate that is used may be greater than $1.0 \times 10^6$ sec$^{-1}$.

Once the baseline for a specific CMP slurry is established, other batches of that CMP slurry may be analyzed for particle agglomeration. In accordance with an implementation of the invention, a batch of the CMP slurry may be analyzed by first conducting rheometric tests on the slurry at ultra high shear rates (402). The rheological behavior of the CMP slurry under analysis may then be compared to the established baseline for that specific CMP slurry (404).

The comparison is to determine whether the rheological behavior of the CMP slurry being analyzed is substantially similar to the established baseline (406). If this is true and the rheological behavior of the CMP slurry being analyzed is indeed similar to the established baseline, a determination may be made that the CMP slurry is still fresh (408). The CMP slurry may then be used in a CMP process (410).

If, however, the Rheological behavior of the CMP slurry being analyzed is substantially different from the established baseline, a determination may be made that the CMP slurry is aged and has particle agglomeration (412). For example, if the viscosity of the CMP slurry is two to tens times higher than the established baseline, a determination may be made that the CMP slurry is aged and suffers from particle agglomeration. Furthermore, if the viscosity of the CMP slurry exhibits strong thickening behavior as the ultra high shear rate is increased, then a determination may be made that the CMP slurry is aged and suffers from particle agglomeration. The aged CMP slurry may then be discarded (414).

In implementations of the invention, a general baseline may be established for a general type of CMP slurry, such as a colloidal silica slurry, and that baseline may be used for all types of that slurry, such as all types of colloidal silica slurries, regardless of brand or manufacturer. In other implementations, baselines may be established that are brand or manufacturer specific. In implementations of the invention, a CMP slurry may be characterized by testing a relatively small sample of the CMP slurry. In other implementations, a CMP slurry may be characterized by testing the entire batch of the CMP slurry.

CMP slurries that may be analyzed by the methods of the invention described herein include, but are not limited to, silica-based, alumina-based, colloidal, or fumed abrasive based slurries for use in CMP processes on oxide, copper, aluminum, shallow trench isolation, barrier layers, and slurries for low-k dielectric materials, among others.

The invention may be implemented in one or a combination of digital electronic circuitry, hardware, firmware, and software. The invention may also be implemented as instructions stored on a machine-readable medium, which may be read and executed by a processing platform to perform the operations described herein. A machine-readable medium may include any mechanism for storing, transmitting, or receiving information in a form readable by a machine (e.g., a computer). For example, a machine-readable medium may include read only memory (ROM); random access memory (RAM); magnetic disk storage media;

optical storage media; flash memory devices; electrical, optical, acoustical or other form of propagated signals (e.g., carrier waves, infrared signals, digital signals, the interfaces that transmit and/or receive those signals, etc.), and others.

The instructions may be implemented as a computer program product, i.e., a computer program tangibly embodied in an information carrier, e.g., in a machine-readable storage device or in a propagated signal, for execution by, or to control the operation of, data processing apparatus, e.g., a programmable processor, a computer, or multiple computers. A computer program may be written in any form of programming language, including compiled or interpreted languages, and it may be deployed in any form, including as a stand-alone program or as a module, component, subroutine, or other unit suitable for use in a computing environment. A computer program may be deployed to be executed on one computer or on multiple computers at one site or distributed across multiple sites and interconnected by a communication network.

Method steps of the invention may be performed by one or more programmable processors executing a computer program to perform functions of the invention by operating on input data and generating output. Method steps may also be performed by, and apparatus of the invention may be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory may be supplemented by, or incorporated in special purpose logic circuitry.

The above description of illustrated implementations of the invention, including what is described in the Abstract, is not intended to be exhaustive or to limit the invention to the precise forms disclosed. While specific implementations of, and examples for, the invention are described herein for illustrative purposes, various equivalent modifications are possible within the scope of the invention, as those skilled in the relevant art will recognize.

These modifications may be made to the invention in light of the above detailed description. The terms used in the following claims should not be construed to limit the invention to the specific implementations disclosed in the specification and the claims. Rather, the scope of the invention is to be determined entirely by the following claims, which are to be construed in accordance with established doctrines of claim interpretation.

The invention claimed is:

1. A method for determining whether a slurry suffers from particle agglomeration and should not be used in a chemical mechanical polishing (CMP) process comprising:
   applying an ultra high shearing force to the slurry, wherein the ultra high shearing force ranges between $1.0 \times 10^5$ sec$^{-1}$ and $5 \times 10^6$ sec$^{-1}$;
   measuring a viscosity of the slurry;
   comparing the measured viscosity to an established baseline viscosity; and
   determining that the slurry suffers from particle agglomeration and should not be used in a CMP process if the measured viscosity is more than two times greater than the established baseline viscosity,
   else determining that the slurry does not suffer from particle agglomeration and should be used in a CMP process.

2. The method of claim 1, wherein the ultra high shearing force ranges between $4.0 \times 10^5$ sec$^{-1}$ and $1.5 \times 10^6$ sec$^{-1}$.

3. The method of claim 1, wherein the slurry comprises a CMP slurry.

4. The method of claim 3, wherein the CMP slurry comprises a silica-based slurry, an alumina-based slurry, a colloidal slurry, or a fumed slurry.

5. The method of claim 1, wherein the ultra high shearing force is applied using an ultra high shear rate rheometer.

6. The method of claim 1, wherein the ultra high shearing force is applied using an ultra high shear rate viscometer.

7. The method of claim 5, wherein the measured viscosity is measured using the ultra high shear rate rheometer.

8. The method of claim 6, wherein the measured viscosity is measured using the ultra high shear rate viscometer.

9. The method of claim 1, further comprising establishing the baseline viscosity prior to comparing the measured viscosity to the established baseline viscosity.

10. The method of claim 9, wherein the establishing of the baseline viscosity comprises:
    applying the ultra high shearing force to a sample of the slurry that does not suffer from particle agglomeration; and
    measuring a viscosity of the sample of the slurry that does not suffer from particle agglomeration.

11. A method for determining whether a slurry suffers from particle agglomeration and should not be used in a CMP process comprising:
    applying a range of ultra high shearing forces to the slurry, wherein the range of ultra high shearing forces falls between $1.0 \times 10^5$ sec$^{-1}$ and $5 \times 10^6$ sec$^{-1}$;
    measuring a range of viscosities of the slurry across the range of ultra high shearing forces;
    comparing the range of viscosities to an established baseline range of viscosities; and
    determining that the slurry suffers from particle agglomeration and should not be used in a CMP process if the measured range of viscosities is more than two times greater than the established baseline range of viscosities,
    else determining that the slurry does not suffer from particle agglomeration and should be used in a CMP process.

12. The method of claim 11, wherein the range of ultra high shearing forces falls between $4.0 \times 10^5$ sec$^{-1}$ and $1.5 \times 10^6$ sec$^{-1}$.

13. The method of claim 11, wherein the slurry comprises a CMP slurry.

14. The method of claim 13, wherein the CMP slurry comprises a silica-based slurry, an alumina-based slurry, a colloidal slurry, or a fumed slurry.

15. The method of claim 11, wherein the ultra high shearing force is applied using an ultra high shear rate rheometer and the measured range of viscosities are measured using the ultra high shear rate rheometer.

16. The method of claim 11, wherein the ultra high shearing force is applied using an ultra high shear rate viscometer and the measured range of viscosities are measured using the ultra high shear rate viscometer.

17. The method of claim 11, further comprising establishing the baseline range of viscosities prior to comparing the range of viscosities to the established baseline range of viscosities.

18. The method of claim 17, wherein the establishing of the baseline range of viscosities comprises:
   applying the range of ultra high shearing forces to a sample of the slurry that does not suffer from particle agglomeration; and
   measuring a range of viscosities of the sample of the slurry across the range of ultra high shearing forces.

19. A method for determining whether a slurry suffers from particle agglomeration and should not be used in a CMP process comprising:
   applying a range of ultra high shearing forces to the slurry, wherein the range of ultra high shearing forces falls between $1.0 \times 10^5$ sec$^{-1}$ and $5 \times 10^6$ sec$^{-1}$;
   measuring a range of viscosities of the slurry across the range of ultra high shearing forces;
   comparing the range of viscosities to an established baseline range of viscosities; and
   determining that the slurry suffers from particle agglomeration and should not be used in a CMP process if the comparison shows that the measured range of viscosities exhibits greater thickening behavior as the ultra high shear rate increases more than the baseline range of viscosities.

20. An apparatus to determine whether a slurry suffers from particle agglomeration and should not be used in a CMP process comprising:
   an ultra high shear rate rheometer capable of producing ultra high shearing forces that fall between $1.0 \times 10^5$ sec$^{-1}$ and $5 \times 10^6$ sec$^{-1}$; and
   an article comprising a machine-readable medium that provides instructions, which when executed by a processing platform, cause said processing platform to perform operations comprising:
      applying an ultra high shearing force to the slurry, wherein the ultra high shearing force ranges from $1.0 \times 10^5$ sec$^{-1}$ to $5 \times 10^6$ sec$^{-1}$;
      measuring a viscosity of the slurry;
      comparing the measured viscosity to an established baseline viscosity; and
      determining that the slurry suffers from particle agglomeration and should not be used in a CMP process if the measured viscosity is more than two times greater than the established baseline viscosity.
      else determining that the slurry does not suffer from particle agglomeration and should be used in a CMP process.

21. The apparatus of claim 20, wherein the operations further comprise establishing the baseline viscosity prior to comparing the measured viscosity to the established baseline viscosity.

22. The apparatus of claim 21, wherein the operation of establishing the baseline viscosity comprises:
   applying the ultra high shearing force to a sample of the slurry that does not suffer from particle agglomeration; and
   measuring a viscosity of the sample of the slurry that does not suffer from particle agglomeration.

23. The apparatus of claim 20, wherein the ultra high shear rate rheometer comprises a slit having a width that ranges from 0.01 mm to 1.0 mm.

24. The apparatus of claim 21, wherein the ultra high shear rate rheometer comprises a capillary tube having a diameter that ranges from 0.1 mm to 2.0 mm and a length that ranges from 5 mm to 20 mm.

* * * * *